Nov. 10, 1970 G. MERRILL Plant Pat. 2,996
PEACH TREE
Filed Jan. 21, 1969
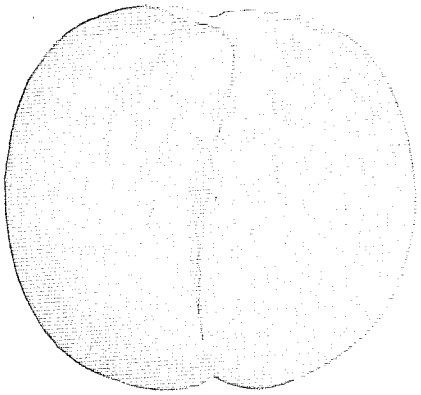
GRANT MERRILL
INVENTOR
Virgil L. Gerard
ATTORNEY

United States Patent Office

Plant Pat. 2,996
Patented Nov. 10, 1970

2,996
PEACH TREE

Grant Merrill, 416 N. Anderson Road,
Exeter, Calif. 93221

Filed Jan. 21, 1969, Ser. No. 792,875
Int. Cl. A01h *5/03*
U.S. Cl. Plt.—43 1 Claim The present invention relates to a peach tree and more particularly to a new and distinct variety thereof broadly characterized by its vigorous, regular bearing tree, and its very early ripening fruit which is highly colored with red over half or more of its surface, round shaped, relatively large for its season and has very few split pits.

The instant variety most nearly resembles Bonjour (U.S. Plant Pat. No. 2,694) but is an improvement thereon in that it bears fruit which is two to five days earlier and more round in shape.

I originated the present variety on a farm formerly owned by me at Red Bluff, Tehama County, Calif., by crossing Blazing Gold (U.S. Plant Pat. No. 1,127) with Gemfree (U.S. Plant Pat. No. 1,409) and then growing the resulting seed by means of embryo culture. I then selected this seedling (Number 57–131 for reference purposes) from a large number of peach trees bearing early ripening fruit of this breeding and similar breeding tested in the San Joaquin Valley of California from 1964 to 1968, by determining from comparison with other early ripening varieties, and consultation with growers that this selection was among the earliest, was the largest and best colored, and had the fewest split pits. The selected seedling (57–131) was then asexually reproduced by budding a number of trees in test plots in Fresno and Tulare Counties, State of California, and the resulting tree and fruit characteristics proved identical to the original tree (57–131).

The accompanying drawing is an oil painting of a characteristic whole fruit of the subject peach tree showing the shape and skin color, and of a characteristic fruit divided at its suture plane showing the flesh color.

Referring now more specifically to the pomological characteristics of this new and distinct variety of peach tree, the following has been observed under the ecological conditions prevailing near Exeter, Tulare County, Calif., and is an outline description thereof. All major color plate identifications are by reference to Maerz and Paul, Dictionary of Color, 1st ed.

TREE

General: Medium size; medium vigorous; vase shaped when pruned.
Productivity: Sets fruit moderately but regularly.
Trunk: Medium size; shaggy gray.
Branches: Medium slender; gray on older branches and brown on younger branches.
Lenticels: Medium size; numerous.
Leaves: Location, from center portion of terminal shoots 30 to 36 inches long; medium size, 4 to 7 inches long, ¾ to 1½ inches wide; lanceolate; tip, accuminate; medium thick; width-length ratio 5 or 6 to 1; class (Meador and Black: Proceedings of the American Society for Horticultural Science, vol. 37, p. 206) 2 and 3; margin crenate; glandular; petiole, medium size; glands, reniform, located at base of leaf and on periole, one to five in number; stipules on young leaves, falling off early; color, upper surface dark green, lower surface light green, veins, very light yellowish green.

FLOWER BUDS

Medium size; plump; free; pubescent.

FLOWERS

Blooms: Early to mid-season about with Elberta (unpatented); moderately abundant; pollen abundant.
Size: Small.
Color: Pink with salmon tinge.

FRUIT

Maturity (when described): Firm to nearing soft ripe, May 30, 1968.
Size: Variable diameter; axially 2⅛ to 2⅝ inches; transverse in suture plane 2⅜ to 3 inches; right angle to suture plane 2¼ to 2¾ inches.
Shape: Variable; generally globose on mature fruit; oval on immature fruit; compressed right angle to suture plane on very ripe fruit.
Suture: A distinct depression which extends from base to near apex but discontinues at apex and has slight depression beyond pistil point.
Dorsal surface: Rounded.
Cavity: Medium abrupt; elongated in suture plane and showing on both sides; depth ¼ to ½ inch; breadth ½ to ¾ inch; yellow ground color with red blush when exposed to the sun.
Base: Rounded to retuse.
Apex: Mucronate; pistil point apical, very short.
Stem: Medium size; about ⅛ inch in diameter; ¼ inch long; adheres frequently to stone.
Skin: Medium thick; medium tough; sweet; tenacious to flesh; under color yellow 9–L–1 with red blush from light red 1–C–11 to darker red blush 6–L–6 with lighter red stripes 1–K–11; pubescence, scant.
Flesh: Color, very light yellow 9–J–1 near stone to light yellow 9–K–5 nearer skin; amygdalin, moderate; juice moderate, rich; texture, generally meaty to melting when soft ripe; fibers, moderate in amount, fine, tender; ripens evenly; flavor, subacid delicate; firmness, when shipping ripe very firm, when soft ripe melting to slightly firmer near stone; good eating quality.

STONE

Generally: Clings to flesh except when fruit is ripened off of the tree, then flesh is free in part from the stone.
Size: Medium to small; 1¼ to 1½ inches long; ⅞ to 1 inch wide; ⅝ to ¾ inch thick.
Form: Generally obovate.
Base: Straight to oblique.
Hilum: Oval.
Apex: Acuminate.
Surface: Irregularly pitted and furrowed; pits generally circular.
Ventral edge: Thick with many fine furrows and with deep groove on each side.
Dorsal edge: Deep groove extending from base half way more or less to apex.
Color: Light tan.
Tendency to split: Slight.
Use: Local and distant fresh markets, eating quality good.

Although my new variety of peach possesses the described characteristics under the growing conditions near Exeter, Tulare County, Calif., having first been observed near Red Bluff, Tehama County, Calif., it is to be understood that variations of the usual magnitude in characteristics incident to the growing conditions, fertilization, pruning and pest control is to be expected.

Having thus described and illustrated my new variety of peach tree, what is claimed is:

1. A new and distinct variety of peach substantially as illustrated and described, which is characterized by a regular bearing tree of good vigor, and very early ripening fruit having high color, large size for its season, round shape and few split pits; and which most closely resembles Bonjour (U.S. Plant Pat. No. 2,694) but is distinguished therefrom primarily by the characteristic of bearing fruit two to five days earlier which is more round in shape.

No references cited.

ROBERT E. BAGWILL, Primary Examiner